(12) United States Patent
Koudil et al.

(10) Patent No.: US 8,518,707 B2
(45) Date of Patent: Aug. 27, 2013

(54) METHOD OF MONITORING ADSORBENT BED BREAKTHROUGH IN A PROCESS FOR PRODUCING ALKYL ESTERS FROM VEGETABLE OR ANIMAL OIL AND FROM AN ALIPHATIC MONOALCOHOL

(75) Inventors: Abdelhakim Koudil, Lyons (FR); Karin Barthelet, Lyons (FR); Laurent Bournay, Chaussan (FR)

(73) Assignee: IFP Energies Novelles, Rueil-Malmaison Cedex (FR)

( * ) Notice: Subject to any disclaimer, the term of this patent is extended or adjusted under 35 U.S.C. 154(b) by 189 days.

(21) Appl. No.: 12/505,835

(22) Filed: Jul. 20, 2009

(65) Prior Publication Data

US 2010/0022019 A1 Jan. 28, 2010

(30) Foreign Application Priority Data

Jul. 22, 2008 (FR) ..................... 08 04153

(51) Int. Cl.
*G01N 33/00* (2006.01)
*B01D 15/08* (2006.01)
*B01D 35/14* (2006.01)

(52) U.S. Cl.
USPC .......................................... 436/131; 436/127

(58) Field of Classification Search
USPC ............... 422/82.05, 103; 436/71, 131, 164, 436/169
See application file for complete search history.

(56) References Cited

U.S. PATENT DOCUMENTS 6,576,044 B1 * 6/2003 Ho et al. .................... 95/102

OTHER PUBLICATIONS

Zhou et al. "Solubility of Multicomponent Systems in the Biodiesel Production by Transesterification of *Jatropha curcas* L. Oil with Methanol." 2006. J. Chem. Eng. Data. vol. 51. pp. 1130-1135.*
Yori et al. "Deglycerolization of Biodiesel Streams by Adsorption Over Silica Beds". 2007. Energy and Fuels. vol. 21. pp. 347-353.*
DeSilva, F. J. "Essentials of Ion Exchange". 1999. 25th Annual WQA Conference.*
Shrestha et al. "Investigation of Biodiesel Quality Sensing Technologies". 2007. Biological and Agricultural Engineering Quarterly Progress Report IV.*

* cited by examiner

*Primary Examiner* — Christine T Mui
(74) *Attorney, Agent, or Firm* — Millen, White, Zelano & Branigan, P.C.

(57) ABSTRACT

A method of monitoring breakthrough of an adsorbent bed consisting for example of ion-exchange resins, used during a stage of purification of an ester stream containing glycerin, obtained for example in a vegetable or animal oil and aliphatic monoalcohol transesterification process, permits the instantaneous detection of the presence of glycerol (glycerin) in the ester stream by arranging a turbidimeter at the adsorbent bed outlet.

8 Claims, 2 Drawing Sheets

METHOD OF MONITORING ADSORBENT BED BREAKTHROUGH IN A PROCESS FOR PRODUCING ALKYL ESTERS FROM VEGETABLE OR ANIMAL OIL AND FROM AN ALIPHATIC MONOALCOHOL

FIELD OF THE INVENTION

The invention relates to an improved method of purifying a mixture of esters and of glycerin.

BACKGROUND OF THE INVENTION

With a view to their use as biofuel, vegetable oil alkyl esters are produced from vegetable oils obtained for example from rapeseed, sunflower, soybean or even palm. Ill-suited for directly feeding modern diesel engines of private cars, vegetable oils essentially consisting of triglycerides have to be converted by means of a transesterification reaction with an alcohol, methanol or ethanol for example, introduced in excess to produce vegetable oil methyl esters (VOMEs) and glycerin.

The current EN 14,214 European standard on biofuels sets maximum methanol, water, free glycerol, mono-, di- and triglyceride contents: 0.2% by mass methanol, 500 mg/kg water, 0.02% by mass free glycerol, 0.8% by mass monoglycerides, 0.2% by mass di- and triglycerides.

Free glycerol, as opposed to bonded glycerol, is defined as a glycerol molecule totally detached from any carbon chain and of formula $C_3H_8O_3$.

Glycerol is referred to as bonded when the functional group of glycerol $C_3H_8O_3$ is alkylated to one or more fatty acid chains giving monoglyceride, diglyceride or triglyceride molecules.

The vegetable and/or animal oils used in this alkyl ester manufacturing process can be any oils known to the person skilled in the art, for example rapeseed, palm, sunflower, soybean, copra, castor oil, as well as fatty substances of animal origin such as tallow.

The alcohol used generally is an aliphatic monoalcohol. Preferably, the alcohol essentially consists of methanol and/or ethanol.

Glycerol is known to be infinitely soluble in water and alcohols, little soluble in ethers and totally insoluble in benzene (Handbook of Chemistry and Physics, $54^{th}$ Edition, 1973-1974), i.e. it is soluble in rather polar media. Glycerol and esters such as methyl esters have very little mutual solubility but methanol acts as a co-solvent. The glycerol content of the ester phase increases with higher temperatures and higher methanol contents.

In order to reach the content allowed by the fuel specification (below 200 ppm), it is necessary to separate the glycerin dissolved in the ester phase.

Depending on the type of method used, this separation is achieved differently. In the methods referred to as homogeneous catalysis methods, as described for example in document EP-B1-0,356,317 or WO-2007/034,067, the purification stage can be carried out through successive water wash operations and passage through ion-exchange resins.

In the Esterfip-H™ process developed by IFP and using a heterogeneous catalyst, separation between the glycerol and the ester produced occurs in several stages. In fact, methanol acting as a co-solubilizing agent for the methyl esters and the glycerol, the alcohol evaporation stage carried out at the reaction section outlet makes part of the glycerol present in the stream, in a proportion ranging between 0.1 and 5% by mass, insoluble. The soluble part represents, at ambient temperature, 500 to 700 ppm mass, the allowable maximum content set by the European standard being 200 ppm mass of free glycerol. Both the insoluble glycerol and part of the soluble glycerol therefore have to be separated. Separation is first performed through gravity decantation in a decanter drum. The ester stream flowing from the decanter is then sent to a coalescer. The glycerin phase stream is withdrawn at the bottom point of the coalescer. Methods allowing these two separation stages to be improved are described in the patent applications filed by the assignee under No. FR-07/04,711 and FR-07/04,715.

It is however necessary to perform a final purification stage by adsorption on solids, ion-exchange resins for example. At the end of this stage, the glycerin content of the ester phase thus meets the fuel specification (below 200 ppm).

The ion-exchange resins used in these stages of final purification of the ester phase operate by alternating adsorption and regeneration cycles.

The adsorbent solids thus are in contact with part of the insoluble glycerin. The properties of these solids are such that they have a very high affinity towards the glycerin contained in the stream to be purified. When this stream predominantly containing ester, partly converted glycerides, methanol traces and soluble and insoluble glycerin passes through the fixed resin bed, the solid captures, i.e. retains, through a "physisorption" phenomenon, the soluble and insoluble glycerin and allows the other molecules to pass through. This solid has sites that attract and retain the glycerin because of their configuration and/or polarity. Each site can however capture only a finite number of glycerin molecules, the other ones present in the ester stream will pass through without being retained. Thus, a glycerin molecule present in the stream to be purified flowing through the bed will be captured by the first unsaturated site it encounters, but it will pass through the bed if it encounters none. Globally, as long as the bed is not saturated, there will be no glycerin in the stream obtained at the resins outlet, but as soon as the bed is saturated, the glycerin content in this stream will increase and become identical to that of the incoming stream to be purified (breakthrough phenomenon). It is then necessary to regenerate the resins, i.e. to remove the glycerin captured by a suitable solvent.

In order to permanently ensure a stream produced without glycerin, meeting the biofuel specifications imposed by the current European standard, the purification zone consists of two adsorbers operating intermittently. While one is in the adsorption phase, the other is regenerated so as to always have a regenerated adsorber when the one working in adsorption mode becomes saturated.

For the specification relative to the glycerin content in the final ester stream to be continuously met, it is thus essential to very finely monitor the breakthrough time, i.e. the time when the bed is saturated and therefore when the glycerin content of the stream produced increases very rapidly and might exceed the glycerin content allowed by the fuel specification. The breakthrough time, i.e. the elapsed time between a quasi-zero glycerin content and the content of the incoming stream, is of the order of 30 minutes in the case of the Esterfip-H™ process.

There are analysis methods that are commonly used to determine the glycerin content of the outgoing stream and therefore to detect the breakthrough time. Gas chromatography can notably be used. This method, described in the EN 14,214 standard, requires a sample preparation of 15 to 30 minutes minimum prior to injection in a chromatogram, then the chromatographic analysis proper is carried out and lasts 2 hours on average.

Another method consists in carrying out glycerin determination with metaperiodate. This reaction is based on a chemical reaction with metaperiodate under controlled pH, one of the reactions products being then determined. This reaction is conducted in the aqueous phase. A water wash operation therefore has to be carried out on the ester sample so as to extract all of the glycerin present, and glycerin determination is performed after decanting in the aqueous phase. Even if determination can be automated, the sequence of these operations (washing+decanting+determination) penalizes the accuracy of the method, which furthermore remains long (between 1 h30 and 2 hours).

The methods and the analysis times currently used are not compatible with fine monitoring, i.e. real-time detection of the breakthrough of the resins and, more generally, of the adsorbent beds. In fact, this involves multiplying costly analyses and, at best, changing adsorbers too late after breakthrough (1 h30 to 2 h thereafter), which implies the production of a quite considerable volume of an off-specification product.

A method allowing detection and/or very fast monitoring, in real time, of the presence of glycerin in the ester phase is therefore needed.

The present invention provides an adsorbent bed breakthrough detection and/or monitoring method that does not involve the aforementioned drawbacks and applies to biodiesel manufacturing processes wherein the glycerin has to be separated from the product obtained.

SUMMARY OF THE INVENTION

The present invention describes a simple and fast method of detecting and/or monitoring the breakthrough of an adsorbent bed used in a process for purifying a mixture of esters and glycerin.

The invention describes the installation in which the method of monitoring the breakthrough of the adsorbent bed used during the stage of purification of a stream of fatty acid alkyl esters is used.

DETAILED DESCRIPTION

Figure 1:
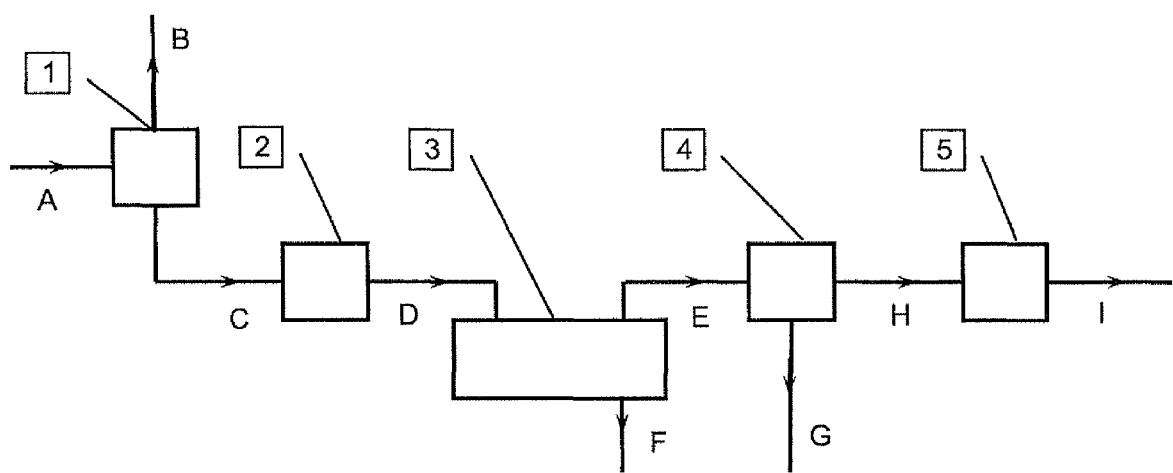
FIG. 1 diagrammatically shows part of the Esterfip-H™ process as described in the prior art.

The present invention describes a method of purifying a mixture of esters and of glycerin on at least one adsorbent bed that captures the glycerin, wherein breakthrough of the bed is detected and/or monitored by measuring the amount of glycerin present in the purified stream by turbidimetry, purification of the ester stream occurring on at least two adsorbent beds arranged in different reactors, one at least being in adsorption mode and one at least in regeneration mode.

Preferably, the mixture of esters to be purified is a mixture of fatty acid alkyl esters from the transesterification of a vegetable or animal oil and of an aliphatic monoalcohol.

The method according to the present invention allows the detection practically, in real time of the precise time of breakthrough of the adsorbent bed and consequently can avoid the production of too large a volume of product that does not meet the fuel specifications.

This method is simple to implement and it requires no prior preparation. In fact, it is not necessary to take samples, as it is the case with the analysis methods used to date. Turbidimetric measurement is directly achieved on a diversion of the installation where the method is implemented: it thus allows to have an instantaneous measurement result.

The turbidimetric measurement is based on the attenuation of a light beam whose wavelengths are essentially in the visible spectrum but can go beyond, notably up to the near infrared. A light beam from a lamp, focussed by a lens system, passes through the medium to be analysed and it is received by a detection system arranged at the opposite end. This beam is processed by a filter that selects the desired measurement domain (UV, visible or IR). A photodiode eventually quantifies the residual light intensity. The attenuation of the incident light beam obeys Beer Lambert's law, and the measurement of this attenuation allows to continuously know the concentration of a liquid, a phase change, or to measure a turbidity.

The turbidity measurement uses the property of a non-dissolved particle of deflecting the light. As previously, a light beam from the transmission module passes through the fluid placed in the measurement volume and possibly encounters particles. These particles are going to deflect all or part of this beam. Photodiodes inclined at a certain angle set by the device manufacturer measure the deflected light intensity and thus evaluate the particle concentration. A photodiode at an angle of 0° could be used for real-time compensation of any change in the colour of the liquid.

The turbidimeter is calibrated prior to carrying out measurements, by any method known to the person skilled in the art, for example by performing concentration measurements by determination with metaperiodate.

Measurement of the amount of glycerin present in the purified stream is achieved by turbidimetry, advantageously after cooling the ester stream to a temperature of at most 20° C., preferably at most 10° C.

The method according to the present invention surprisingly allows to detect an amount of glycerin below the solubility threshold conventionally accepted since the turbidimeter detects an amount of glycerin below 200 ppm.

Esters being not particularly polar, the solubility limit of the glycerin in the ester phase is relatively low, as confirmed by some studies in the literature (D. S. Negi, F. Sobotka, T. Kimmel, G. Wozny, R. Schomäcker, *Ind. Eng. Chem. Res.*, 2006, 45, 3693-3696, H. Zhou, H. Lu, B. Liang, *J. Chem. Eng. data*, 2006, 51, 1130-1135 and A. E. Andreatta, L. M. Casas, P. Hegel, S. B. Bottini, E. A. Brignole, *Ind. Eng. Chem. Res.*, 2008, in press) conducted on ternary ester/methanol/glycerol systems.

However, the true solubility limit of glycerol in esters is not easily determined from the data published insofar as the results recorded relate to mixtures with large amounts of methanol acting as a co-solubilizing agent for glycerol in ester and as the lack of experimental points for low methanol contents does not allow the extrapolation of the ternary diagrams to a zero methanol value.

It has therefore been necessary to determine it. Experimental measurements were therefore carried out on the vegetable rape oil methyl ester/glycerol system. The solubility measurements consisted in bringing together ester and glycerol in excess so as to obtain two distinct phases and to be sure the ester phase is saturated with glycerol, in a thermostat-controlled oven, at the selected temperature, long enough for equilibrium to be reached. A sample is then taken from the ester phase and analysed by gas chromatography according to the method of determining glycerol in ester described in the EN 14,214 standard. All of these values are given in Table 1 hereafter.

TABLE 1

| T (° C.) | $C_{limit}$(glycerol) (ppm) |
|---|---|
| 20 | 320 |
| 43 | 484 |
| 61 | 813 |
| 80 | 1233 |

BRIEF DESCRIPTION OF FIGURES

Figure 2:
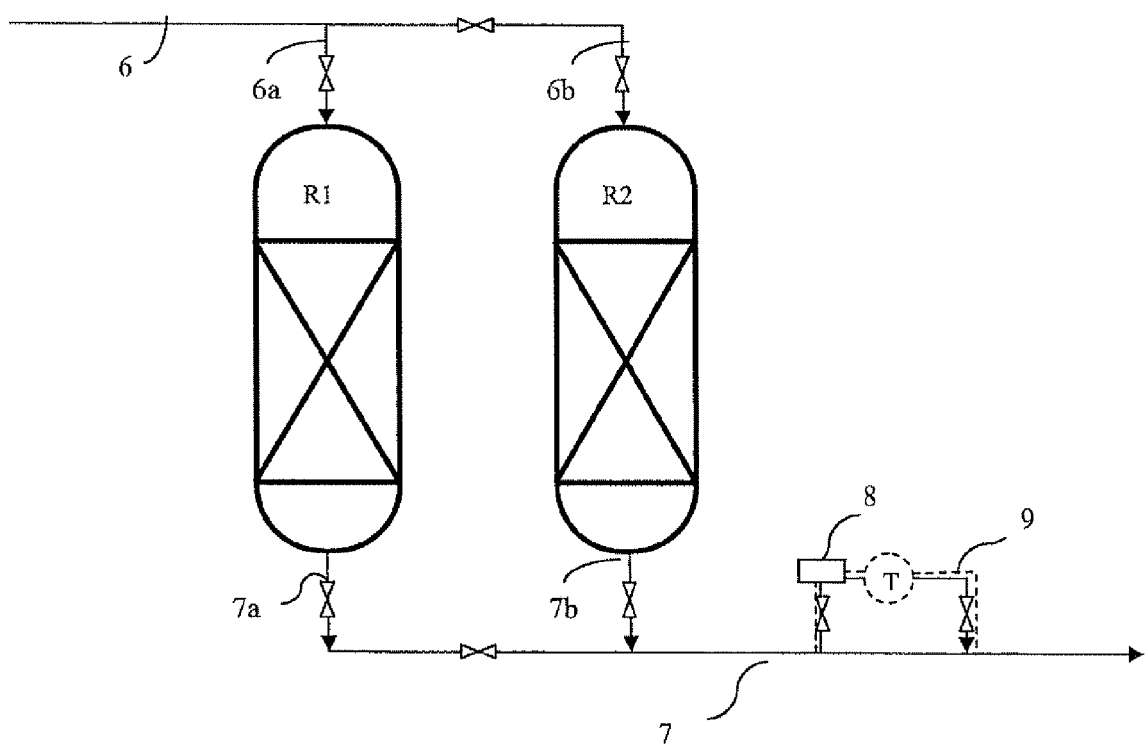
FIG. 2 diagrammatically shows the part of the Esterfip-H™ process wherein the purification method according to the present invention is carried out.

The present invention can now be described in connection with FIGS. 1 and 2 relative to a vegetable or animal oil transesterification method with an aliphatic monoalcohol, wherein FIG. 1 is a block flowsheet of a general process of producing the esters and FIG. 2 is a schematic flowsheet of the improvement of the invention.

In the method diagrammatically shown in FIG. 1 and as described in the prior art, stream A at the reaction section outlet predominantly contains methyl esters, methanol, glycerol and partly converted glycerides (monoglycerides, diglycerides and triglycerides), as well as traces of water, an impurity present in the feedstock. Zone (1) corresponds to the zone where the methanol evaporation stage is carried out and zone (2) is advantageously a heat exchanger. Separation of the glycerin is performed in a separation zone that advantageously operates in several stages conducted in equipments (3) to (5) respectively corresponding to a decanter drum (3), a coalescer (4) and an adsorption zone on solids (5) (or adsorbents), corresponding to the zone referred to as "purification zone" in the present invention.

FIG. 2 shows purification zone (5) where the adsorbent bed breakthrough detection and/or monitoring method according to the invention is used and it corresponds to an improvement of the Esterfip-H™ process.

Purification of the ester stream is carried out on at least two adsorbent beds arranged in different reactors, one at least being in adsorption mode and one at least in regeneration mode. When the measurement of the amount of glycerin present in the stream at the outlet of a reactor R1 working in adsorption mode reaches the set value, said reactor is switched to the regeneration mode, and the incoming ester stream to be purified is sent to another adsorbent bed that can work in adsorption mode.

The alkyl ester stream to be purified circulates in lines (6), then (6a) if it has to be sent to reactor R1 (respectively (6b) if it has to be sent to reactor R2).

The resins commonly used as adsorbents are acidic resins (sulfonic groups) in sodic form, macroporous, based on the cross-linked styrene-divinylbenzene copolymer. The preferential interaction between the resins and the adsorbate molecules is the establishment of hydrogen bonds either between the oxygen or sulfur atoms of the sulfonic group of the resin and hydrogen atoms of the adsorbate molecules, or between the sodium cations of the resins and heteroelements such as the oxygen atoms of the adsorbate molecules. This type of resin consequently takes up especially polar compounds and more particularly those having OH functions. It is therefore totally suited for the adsorption of glycerol, all the more so since it is in the ester that contains only traces of competitors such as water or alcohols.

The adsorbents used in reactors R1 and R2 are selected from among ion-exchange resins, preferably acidic and most preferably in the sodium form, silica gel, aluminas, silica-aluminas, or activated charcoals having oxygen-containing groups on their surface.

Any type of mesoporous and preferably macroporous solids, functionalized in such a way that a particular affinity is established between its functions and the OH groups of the glycerin so as to preferentially retain it and having a sufficient mechanical strength, can be considered.

At the outlet of reactors R1 and R2, the ester stream, normally purified, is sent to the gasoline pool through a line (7). In this line, the ester stream is generally at a temperature on the order of about 60° C.

Line (9) is a diversion line starting from line (7). Inside line (7), cooling means can be suited, if need be, to cool the purified ester stream for example. Thus, the ester stream can be cooled down to about 20° C., preferably to about 10° C.

Turbidimeter T is arranged at the outlet of the reactor(s). If the turbidimeter is arranged within line (7), measurement can consequently be performed on a cooled ester stream. The solubility of the glycerin in the alkyl esters is inversely proportional to the temperature (see Table 1). Decreasing the temperature in line (7) thus speeds up the possibility of detecting the insoluble glycerin, and lowering the solubility threshold allows the soluble glycerin to be detected.

The measurements performed by means of the turbidimeter at regular time intervals consequently allow to detect breakthrough of the adsorbents and progressive loading of the stream of esters produced with glycerin. In fact, the presence of glycerin in the ester phase modifies the optical characteristics of the ester. Locally, even before the appearance of a glycerin droplet, an oversaturation detectable with the turbidimeter occurs.

Thus, there is a threshold value for the glycerin concentration in the stream of fatty acid alkyl esters to which the turbidimeter responds. The turbidimeter emits no signal below this threshold value. A response is observed on the turbidimeter from approximately 60 ppm glycerin present in the ester stream. This threshold value remains lower than the glycerin concentration permitted according to standards currently in force.

Obtaining a response on the turbidimeter (threshold value reached) means that the adsorbent bed used is saturated and at end of cycle: it has to be switched to the regeneration mode, which consists in removing the glycerin captured by a suitable solvent. Consequently, the incoming alkyl ester stream that is to be subjected to the purification stage is sent to another adsorbent bed working in adsorption mode.

If the measurement performed for example at the outlet of reactor R1 working in adsorption mode reaches or exceeds the specification, or more generally the set value given by the operator, and if it notably exceeds the value of 200 ppm glycerin required by the standard, the beds are switched: reactor R1 switches to the regeneration mode and the incoming alkyl ester stream to be subjected to the purification stage is sent to the other adsorbent bed R2 working in adsorption mode.

It is possible to convert the turbidimeter measurement to an analog signal that can automatically trigger the adsorbent bed switch from a threshold level defined by the user.

Thus, the breakthrough monitoring method according to the present invention is a very flexible technique allowing, if necessary, continuous monitoring of the glycerin concentration in the ester stream. Operators can carry out as many analyses as they wish, and the acquisition frequency can be adjusted as one wants. Thus, this frequency is relatively low at the start of the adsorbent bed working cycles, the breakthrough risk being low. On the other hand, this frequency is quasi-continuous towards cycle end for fine breakthrough detection.

Another advantage of the present invention thus is the improvement of the product quality by avoiding the off-specification periods inherent in the analysis time. Furthermore, the operation is thus made more reliable by preventing possible human errors linked with sampling, handling and determination of products during analyses.

It also allows a reduction in the laboratory and supervision costs by decreasing the monitoring and analysis duties involved, as well as the operation of the industrial tool because refining breakthrough monitoring allows to optimize the switch threshold, and therefore to make the best use of the adsorption capacity of the solid while respecting the desired quantity.

The present invention also describes an installation comprising a zone for transesterification of vegetable or animal oil by an aliphatic alcohol, a zone of evaporation of the alcohol present in the effluent coming from the transesterification zone, possibly a thermal exchange zone, a glycerin separation zone including a zone of purification on adsorbents, an installation wherein:

a line (6) carries a stream H of fatty acid alkyl esters and glycerin, the purification zone comprises at least two fixed adsorbent beds arranged in at least two reactors R1 and R2, one at least working in adsorption mode and one at least in regeneration mode, a line (7a, 7b) at the reactors outlet on which part of the ester stream is diverted through a line (9) and a turbidimeter is arranged to perform the measurements.

The installation also comprises a device (8) for controlling the temperature of the stream of line (9) located upstream from turbidimeter (T) in the direction of circulation of said stream.

Advantageously, line (9) is surrounded with a device suited for cooling the ester stream circulating within said line.

The installation can also comprise a device for triggering the bed switch, said device being actuated when the turbidimeter gives a measurement of the amount of glycerin at least equal to the set value.

EXAMPLE

Monitoring of the glycerin concentration in the ester produced according to the Esterfip-H process after passage through acidic resins with sulfonic groups of Lewatit Monoplus SP 112 type marketed by Lanxess (Bayer), in form of monodisperse balls, was conducted using a TF16 type turbidimeter manufactured by Optek. The angle of inclination of the photodiodes is in this case 11°. Measurement being performed by taking samples at different times from the initial time, it allows to monitor the quality of this ester. All of these measurements were carried out at ambient temperature.

In order to calibrate the measurements obtained, concentration measurements were performed by means of the known metaperiodate determination method.

The table below gives the values obtained:

| Time (h) | Concentration determined with the metaperiodate technique (ppm) | Concentration measured with the turbidimeter (u.a.) |
|---|---|---|
| T0 | 55 | 0 |
| T0 + 1 | 61 | 0.001 |
| T0 + 6 | 130 | 0.038 |
| T0 + 9 | 191 | 0.066 |

It can be observed that there is a threshold effect: the turbidimeter is blind up to a concentration close to sixty ppm. Then, it measures quite significant values. Since the specification imposed by the current European standard is of the order of 200 ppm, a turbidimeter is thus quite able to provide continuous monitoring of the glycerin concentration in the ester and to detect an end of cycle of the resins so as to switch from one adsorbent bed to the other.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 08/04.153, filed Jul. 22, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of purifying a mixture of esters and of glycerin, comprising subjecting the mixture to an adsorbent bed that captures glycerin, purification of the mixture occurring on at least two adsorbent beds arranged in different reactors, one at least being in adsorption mode and one at least in regeneration mode, wherein breakthrough of the bed is continuously detected and/or monitored by measuring the amount of glycerin present in the purified stream by turbidimetry, such that when the measurement of the amount of glycerin present in the stream at the outlet of a reactor R1 working in adsorption mode reaches a set value, said reactor is switched to the regeneration mode, and the incoming ester stream to be purified is sent to another adsorbent bed that can work in adsorption mode, measurement of the amount of glycerin present in the purified stream is achieved by turbidimetry after cooling the ester stream from a temperature higher than 20° C. to a temperature of at most about 20° C., the turbidimeter measurement is converted to an analog signal and it automatically triggers an adsorption bed switch.

2. A method as claimed in claim 1, wherein the adsorbent is selected from among ion-exchange resins, silica gel, aluminas, silica-aluminas, and activated charcoals having oxygen-containing groups on their surface.

3. A method as claimed in claim 1, wherein when the measurement of the amount of glycerin present in the stream at the outlet of a reactor R1 working in adsorption mode reaches a set value, said reactor is switched to the regeneration mode, and the incoming ester stream to be purified is sent to another adsorbent bed that can work in adsorption mode.

4. A method as claimed in claim 1, wherein the mixture of esters to be purified is a mixture of fatty acid alkyl esters from the transesterification of a vegetable or animal oil and of an aliphatic monoalcohol.

5. A method according to claim 1, wherein the adsorbent is an ion exchange resin in the acid form.

6. A method according to claim 1, wherein the adsorbent is an ion exchange resin in the sodium form.

7. A method according to claim 1, wherein the ester stream is cooled to at most about 10° C.

8. A method according to claim 1, wherein said temperature higher than 20° C. is 60° C.

\* \* \* \* \*